(12) United States Patent
Chen et al.

(10) Patent No.: US 10,902,949 B2
(45) Date of Patent: Jan. 26, 2021

(54) CALL SYSTEM FOR PATIENT

(71) Applicant: Shenzhen Polytechnic, Shenzhen (CN)

(72) Inventors: Meifen Chen, Shenzhen (CN); Bo Wu, Shenzhen (CN); Wenli Li, Shenzhen (CN); Tiefeng Cai, Shenzhen (CN)

(73) Assignee: Shenzhen Polytechnic, Shenzhen (CN)

( * ) Notice: Subject to any disclaimer, the term of this patent is extended or adjusted under 35 U.S.C. 154(b) by 0 days.

(21) Appl. No.: 16/801,033

(22) Filed: Feb. 25, 2020

(65) Prior Publication Data
US 2020/0194118 A1 Jun. 18, 2020

Related U.S. Application Data

(63) Continuation of application No. PCT/CN2018/101615, filed on Aug. 22, 2018.

(30) Foreign Application Priority Data

Aug. 25, 2017 (CN) .......................... 2017 1 0747086

(51) Int. Cl.
*A61B 5/11* (2006.01)
*G16H 40/67* (2018.01)
(Continued)

(52) U.S. Cl.
CPC ............... *G16H 40/67* (2018.01); *A61F 4/00* (2013.01); *G06F 3/012* (2013.01); *G06F 3/0482* (2013.01);
(Continued)

(58) Field of Classification Search
CPC .......... G06F 3/013; G06F 3/012; G06F 3/017; G06F 1/163; G06F 3/0482;
(Continued)

(56) References Cited

U.S. PATENT DOCUMENTS

2017/0031538 A1\* 2/2017 Andersson ........... G02B 27/017

FOREIGN PATENT DOCUMENTS

| CN | 101566874 A | 10/2009 |
|----|-------------|---------|
| CN | 204814294 U | 12/2015 |

(Continued)

OTHER PUBLICATIONS

International Search Report and Written Opinion with English Translation of ISR, cited in PCT/CN2018/101615 dated Nov. 17, 2018, 17 pages.

*Primary Examiner* — Benyam Haile
(74) *Attorney, Agent, or Firm* — Cooper Legal Group, LLC

(57) ABSTRACT

The present disclosure discloses a call system for a patient. The call system for the patient comprises a head-mounted device, a head motion detection module, an eyelid blinking detection module, a patient display screen, and a nurse station display screen. The head motion detection module collects relative changes of a head position through an aerial attitude sensor. The eyelid blinking detection module collects a movement distance and a movement duration of an eyelid through a photoelectric motion sensor. When the movement distance of the eyelid reaches a preset distance and the movement duration of the eyelid is longer than a preset duration, a confirmation command is generated to select one of multiple call services in a scroll menu, and the one of the multiple call services selected by the patient is sent to the nurse station display screen by a wired network or a wireless network.

9 Claims, 2 Drawing Sheets

(51) Int. Cl.
*G16H 80/00* (2018.01)
*A61F 4/00* (2006.01)
*G06F 3/01* (2006.01)
*G06F 3/0482* (2013.01)
*G06F 3/0485* (2013.01)
*G08B 5/22* (2006.01)
*G06F 3/0488* (2013.01)

(52) U.S. Cl.
CPC ........... *G06F 3/0485* (2013.01); *G08B 5/222* (2013.01); *G16H 80/00* (2018.01); *A61B 5/1103* (2013.01); *A61B 5/1114* (2013.01); *G06F 3/0488* (2013.01)

(58) Field of Classification Search
CPC ... G06F 3/04842; A61B 5/6803; A61B 5/163; A61B 5/1103; A61B 5/0002
See application file for complete search history.

(56) References Cited

FOREIGN PATENT DOCUMENTS

| | | |
|---|---|---|
| CN | 105260017 A | 1/2016 |
| CN | 107616797 A | 1/2018 |
| JP | 2006055388 A | 3/2006 |
| JP | 2016154638 A | 9/2016 |

\* cited by examiner

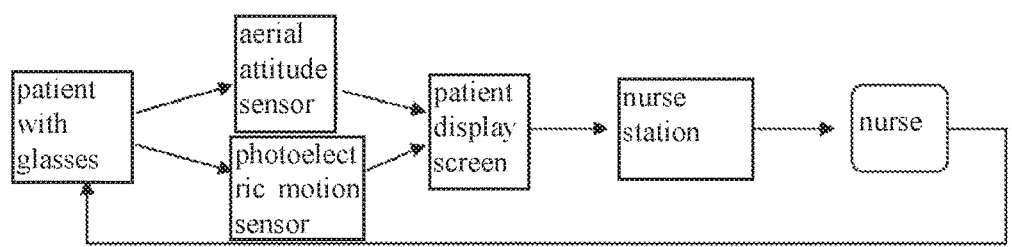
Fig. 1
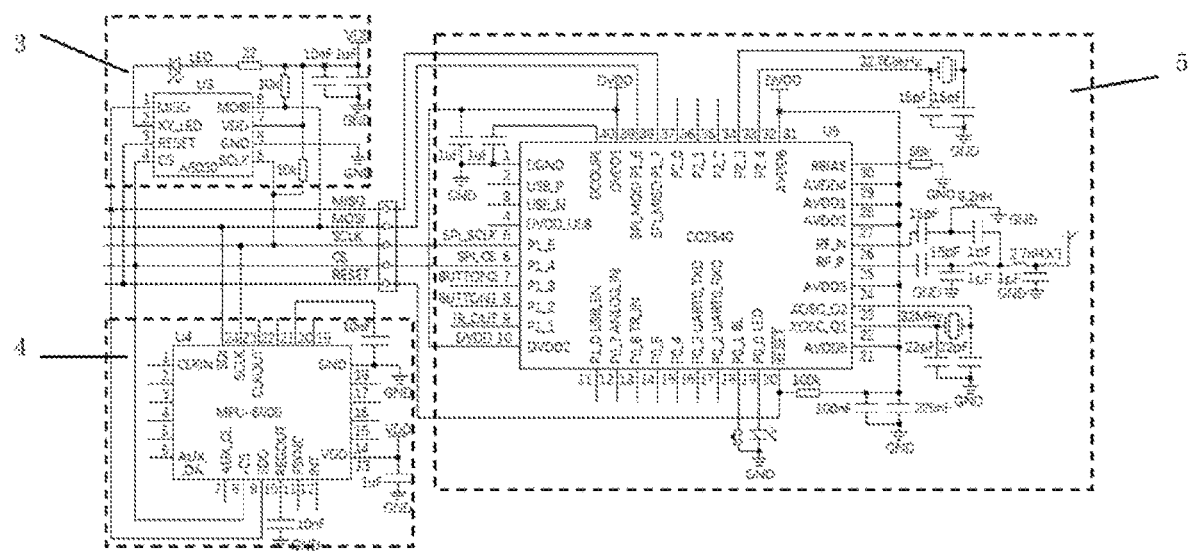
Fig. 2
Fig. 3

CALL SYSTEM FOR PATIENT

RELATED APPLICATIONS

This application is a continuation of and claims priority to PCT Patent Application PCT/CN2018/101615, filed on Aug. 22, 2018, which claims priority to Chinese Patent Application 201710747086.8, filed on Aug. 25, 2017. PCT Patent Application PCT/CN2018/101615 and Chinese Patent Application 201710747086.8 are incorporated herein by reference.

FIELD OF THE DISCLOSURE

The present disclosure relates to a call system for a patient, and in particular relates to a call system for a critically ill patient.

BACKGROUND OF THE DISCLOSURE

A call system is an emergency call tool used by patients to request medical staff for diagnosis or care. It quickly transmits requests of the patients to the doctor or nurse on duty. Existing call systems are mainly implemented by the patient pressing a button. It is not suitable for patients who have difficulty moving. For critically ill patients, the single-button call system does not enable medical staff to quickly understand what kind of care the patient needs. After receiving the call signal, the medical staff must further communicate with the patient to confirm the specific needs of the patient, resulting in work efficiency being low. Even if there is a voice call system for patients and medical staff to communicate in real time, it is not suitable for critically ill patients who have obstacles in verbal communication and who are extremely weak and unable to verbally communicate normally. At the same time, the voice transmissions will affect other patients.

BRIEF SUMMARY OF THE DISCLOSURE

The present disclosure provides a call system for a patient to solve deficiencies of complicated structures of the existing techniques.

In order to solve the aforementioned technical problems, a technical solution of the present disclosure is as follows.

A call system for a patient comprises a head-mounted device, a call system body, a patient display screen, and a nurse station display screen. The call system body comprises a head motion detection module, an eyelid blinking detection module, a communication module, and a power supply module. The head motion detection module collects relative changes of a head position through an aerial attitude sensor, first signals generated based upon the relative changes of the head position are sent to the patient display screen through a Bluetooth module of the communication module so that a cursor of the patient display screen changes synchronously, the cursor is configured to wake up the patient display screen and to activate a scroll menu. The eyelid blinking detection module collects a movement distance and a movement duration of an eyelid through a photoelectric motion sensor, second signals generated based upon the movement distance and the movement duration of the eyelid are sent to the patient display screen through the Bluetooth module of the communication module. The patient display screen is disposed on a patient bed and is above a head of the patient. The power supply module supplies power to the head motion detection module, the eyelid blinking detection module, and the communication module. When the movement distance of the eyelid reaches a preset distance and the movement duration of the eyelid is longer than a preset duration, a confirmation command is generated to select one of multiple call services in the scroll menu, and the one of the multiple call services selected by the patient is sent to the nurse station display screen by a wired network or a wireless network.

In another preferred embodiment, the communication module sends the signals generated based upon the relative changes of the head position collected by the head motion detection module and the signals generated based upon the movement distance and the movement duration of the eyelid collected by the eyelid blinking detection module to the patient display screen through the Bluetooth module, the patient display screen is woken up, the scroll menu is activated, and the one of the multiple call services is selected.

In another preferred embodiment, the head-mounted device comprises glasses, a hat, an earphone, a hair clip, a hair pin, or a headband, and at least a part of the call system body is detachably disposed on the head-mounted device.

In another preferred embodiment, the call system body comprises a charging port, a power switch, an eyelid blinking detection sampling port, a Bluetooth code switch, a Bluetooth code indicator, and a head movement detection sampling port, the charging port, the power switch, the Bluetooth code switch, and the Bluetooth code indicator are disposed on a side of the call system body, and the eyelid blinking detection sampling port is disposed on a second side of the call system body directly facing an eye of the patient.

In another preferred embodiment, the head-mounted device comprises glasses, the glasses have a frame and temples, a lower end of the call system body comprise a connection bracket, and the connection bracket is detachably disposed on at least one of the frame or the temples.

In another preferred embodiment, the first signals generated based upon the relative changes of the head position comprise at least one of a head up signal, a head down signal, a head left signal, a head right signal, or a head inclined signal.

In another preferred embodiment, a model of the aerial attitude sensor is MPU6000. The aerial attitude sensor comprises an eighth pin, a ninth pin, a twenty-third pin, a twenty-fourth pin, a tenth pin, a thirteenth pin, an eighteenth pin, and a twentieth pin. The eighth pin is connected to the Bluetooth module for serial peripheral interface (SPI) chip selection. The ninth pin is connected to the Bluetooth module to output SPI serial data. The twenty-third pin is connected to the Bluetooth module to achieve an SPI serial clock. The twenty-fourth pin is connected to the Bluetooth module to receive SPI serial data. The tenth pin is connected to a calibration filter capacitor. The thirteenth pin is a first power supply terminal connected to the power supply module. The eighteenth pin is power grounded, and the twentieth pin is connected to a capacitor of a charge pump.

In another preferred embodiment, a model of the photoelectric motion sensor is CC2540. The photoelectric motion sensor comprises a first pin, a second pin, a third pin, a fourth pin, a fifth pin, a sixth pin, a seventh pin, and an eighth pin. The first pin is connected to the Bluetooth module to output serial peripheral interface (SPI) serial data. The third pin is connected to the Bluetooth module for resetting the photoelectric motion sensor. The fourth pin is connected to the Bluetooth module for SPI chip selection. The fifth pin is connected to the Bluetooth module to achieve an SPI serial clock. The eighth pin is connected to the Bluetooth module to receive SPI serial data. The second pin is a photodiode input terminal. The sixth pin is power grounded. The seventh pin is a second power terminal connected to the power supply module.

In another preferred embodiment, the patient display screen is a liquid crystal display (LCD) screen with a touch mode and a cursor mode, the touch mode uses a window menu to display the multiple call services for medical staff, the cursor mode uses the scroll menu for the patient.

In another preferred embodiment, a model the Bluetooth module is CC2540. The photoelectric motion sensor and the aerial attitude sensor communicate through a serial peripheral interface (SPI) serial port of the Bluetooth module The Bluetooth module comprises a first pin, a tenth pin, a thirty-ninth pin, a fortieth pin, a twenty-first pin, a twenty-fourth pin, a twenty-seventh pin, a twenty-eighth pin, a twenty-ninth pin, a thirty-first pin, a fifth pin, a sixth pin, a thirty-seventh pin, a thirty-eighth pin, a twentieth pin, a twenty-second pin, a twenty-third pin, a thirty-second pin, a thirty-third pin, a twenty-fifth pin, a twenty-sixth pin, an eighteenth pin, a nineteenth pin, and a thirtieth pin. The first pin is digital grounded. The tenth pin and the thirty-ninth pin are digital power terminals. The fortieth pin is power decoupled. The twenty-first pin, the twenty-fourth pin, the twenty-seventh pin, the twenty-eighth pin, the twenty-ninth pin, and the thirty-first pin are analog power terminals. The fifth pin, the sixth pin, the thirty-seventh pin, and the thirty-eighth pin are SPI serial ports. The twentieth pin is a reset terminal. The twenty-second pin and the twenty-third pin are connected to a 32 MHz crystal oscillator. The thirty-second pin and the thirty-third pin are connected to a 32.768 KHz crystal oscillator. The twenty-fifth pin and the twenty-sixth pin are antenna terminals. The eighteenth pin is a code switch. The nineteenth pin is an indicator terminal. The thirtieth pin is reference current terminal.

In another preferred embodiment, the power supply module comprises a linear charge controller MCP73831, a voltage regulator RT9193, a common cathode diode, a light emitting diode, a power switch, and a battery interface. The linear charge controller comprises a first pin, a second pin, a third pin, a fourth pin, a sixth pin, a seventh pin, and an eighth pin. The first pin of the linear charge controller and the second pin of the linear charge controller are series connected and then connected to a power supply and a first end of a first capacitor. A second end of the first capacitor is grounded so that input filtering is achieved. The third pin is series connected to a first resistor and the light emitting diode and then is series connected with the fourth pin and is power grounded. The sixth pin is series connected to the seventh pin and the eighth pin through a second capacitor so that output filtering is achieved. The common cathode diode is configured to charge and supply power at the same time. The light emitting diode is a charging indicator. The power switch is configured to switch the call system body to be opened and to be closed. The battery interface is configured to connect to a battery. The voltage regulator and peripheral circuits define a voltage regulator circuit. The voltage regulator comprises a first pin and a second pin. The first pin of the voltage regulator is connected to two third capacitors connected in parallel and a first end of a second resistor. A second end of the second resistor is connected to a fourth power supply terminal so that the output filtering is achieved. The second pin of the voltage regulator is connected to two fourth capacitors connected in parallel so that input filtering is achieved.

The technical solution of the present disclosure has the following advantages: the present disclosure help the patient to call medical staff through head motion and eyelid blinking. As an auxiliary assembly, the head-mounted device is convenient to carry, and the at least a part of the call system body can be removed and installed in different head-mounted devices. The head-mounted device has a wide applicable range, and it is applicable to many life scenarios. Compared with the existing solution for pressing a button to make a call by the patient, the present disclosure is adaptable for critically ill patients who have difficulty moving, the specific needs of the call are clear, and the call system helps to improve work efficiency of the medical staff. Compared with the existing verbal call systems for communicating with the medical staff in real time, the technical solution can specify specific needs without language inputting. It is suitable for critically ill patients who have obstacles in verbal communication and who are extremely weak and unable to verbally communicate normally. At the same time, the voice transmissions will affect other patients, which is void with the technical solution. The present disclosure uses Bluetooth communication to achieve calling. The patients are free from limitations of traditional wired communications and have a higher degree of freedom.

BRIEF DESCRIPTION OF THE DRAWING

The present disclosure will be further described below with the combination of the accompanying drawings together with the embodiments. However, the call system for the patient of the present disclosure will not be limited to the embodiments.

FIG. 1 illustrates a diagram of a working principle of the present disclosure.

FIG. 2 illustrates a schematic diagram of a circuit of a call system for a patient of a preferred embodiment of the present disclosure;

FIG. 3 illustrates a schematic diagram of a circuit of a power supply module of the preferred embodiment of the present disclosure;

DETAILED DESCRIPTION OF THE EMBODIMENTS

Embodiment 1

Referring to FIG. 1, a working principle of a call system for a patient of the present disclosure is to convert relative changes of a head position and a movement distance and a movement duration of an eyelid into electrical signals, then wirelessly send the electrical signals to a patient display screen (i.e., a display screen of the critically ill patient). A selected need of the patient, selected from a menu of multiple call services, is transmitted to a nurse station display screen (i.e., a display screen of a nurse station) through a wired network or a wireless network, and medical staff takes care of the patient according to the selected need.

Figure 4:
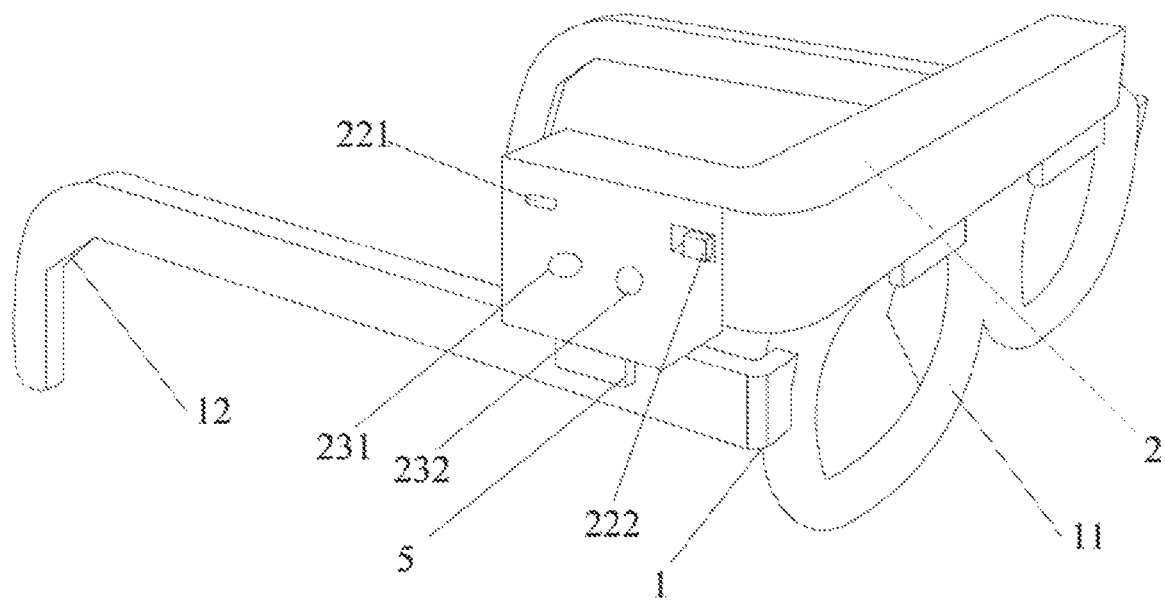
FIG. 4 illustrates a first schematic view of glasses of the preferred embodiment of the present disclosure.
Figure 5:
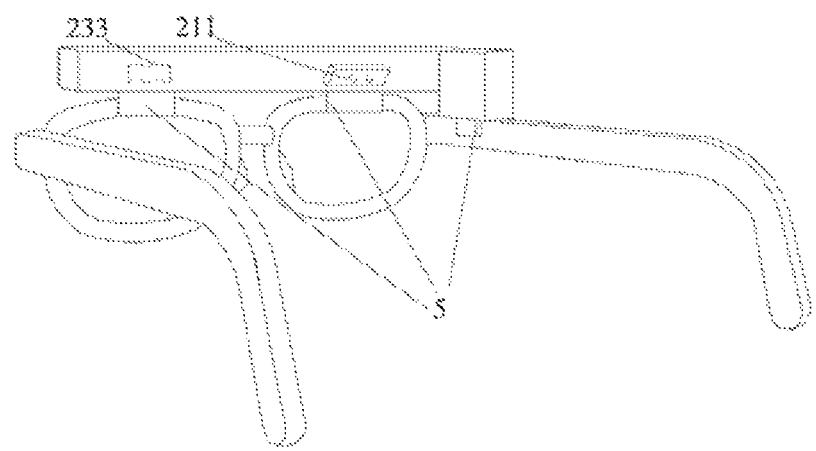
FIG. 5 illustrates a second schematic view of the glasses of the preferred embodiment of the present disclosure.

Referring to FIG. 4 and FIG. 5, a call system for a patient of the present disclosure comprises a head-mounted device and a call system body configured to assist with the care of a critically ill patient. In this embodiment, the head-mounted device comprises glasses 1, and the glasses 1 comprise a frame 11 and temples 12. The call system body 2 is detachably connected to an upper end of the frame 11 and the temples 12 through a bracket 5. The call system body 2 comprises a charging port 221, a power switch 222, an eyelid blinking detection sampling port 211, a Bluetooth code switch 231, a Bluetooth code indicator 232, and a head movement detection sampling port 233. The charging port 221, the power switch 222, the Bluetooth code switch 231, and the Bluetooth code indicator 232 are disposed on a first side of the call system body 2, while the eyelid blinking detection sampling port 211 is disposed on a second side of the call system body 2 directly facing an eye of the patient. This solution is adaptable for various glasses of different standards and sizes, different uses, and in different scenarios.

The call system body 2 comprises a head motion detection module 3, an eyelid blinking detection module 4, a communication module 5, and a power supply module 6. The head motion detection module 3 collects the relative changes of the head position through an aerial attitude sensor, and first signals are generated based upon the relative changes of the head position. The first signals comprise at least one of a head up signal, a head down signal, a head left signal, a head right signal, or a head inclined signal. The first signals generated based upon the relative changes of the head position are sent to a computer through the communication module 5. A cursor on a patient display screen of the computer changes synchronously based on the first signals so that the patient display screen is woken up and a scroll menu is activated. The eyelid blinking detection module 4 collects the movement distance and movement duration of the eyelid through a photoelectric motion sensor. The communication module 5 sends second signals generated based upon the movement distance and movement duration of the eyelid to the computer. When the movement distance of the eyelid reaches a preset distance corresponding to a closed eye and the movement duration is longer than a preset duration corresponding to a duration longer than a typical eye blink, a confirmation command is generated to select one of multiple, different call services of the scroll menu, resulting in the computer receiving a command. The communication module 5 sends the first signals generated based upon the relative changes of the head position collected by the head motion detection module 3 and the second signals generated based upon the movement distance and movement duration of the eyelid collected by the eyelid blinking detection module 4 to the computer through a Bluetooth module to wake up the patient display screen of the computer and activate the scroll menu, and the call services of the scroll menu is selected. The patient display screen transmits the call service selected by the patient by a wired network or a wireless network to the nurse station display screen for medical personnel to view and timely take care of the patient according to the call service selected by the patient. The power supply module 6 supplies power to the head motion detection module 3, the eyelid blinking detection module 4, and communication module 5.

In this embodiment, a schematic diagram of a circuit of the call system is shown in FIG. 2. The circuit comprises three integrated circuits, a photoelectric motion sensor A5030, an aerial attitude sensor MPU6000, and a Bluetooth module CC2540.

The photoelectric motion sensor A5030 and peripheral components constitute the eyelid blinking detection module 4, which is used to implement the patient display screen confirmation command, and select the call service in the scroll menu. The photoelectric motion sensor A5030 comprises a first pin, a second pin, a third pin, a fourth pin, a fifth pin, a sixth pin, a seventh pin, and an eighth pin. The first pin is the serial data output terminal and is connected to the thirty-seventh pin of the Bluetooth module CC2540 to achieve SPI serial data output. The third pin is the reset terminal and is connected to the twentieth pin of the Bluetooth module CC2540 for resetting the photoelectric motion sensor A5030. The fourth pin is connected to the sixth pin of the Bluetooth module CC2540 to implement the SPI chip selection, the fifth pin is connected to the fifth pin of the Bluetooth module CC2540 to implement (i.e., achieve) the SPI serial clock, the eighth pin is connected to a thirty-eighth pin of the Bluetooth module CC2540 to receive SPI serial data input. The second pin is a photodiode input terminal, the sixth pin is power grounded, and the seventh pin is a second power terminal connected to the power supply module 6. When the upper eyelid of the patient blinks, the photoelectric motion sensor A5030 collects the movement distance and movement duration of the eyelid movement distance of the eyelid reaches a preset distance corresponding to closed eye and the movement duration is greater than a preset duration, such as greater than 500 milliseconds, the confirmation key is considered valid (i.e., the confirmation key is selected) to scroll the screen to select different services in the menu.

The aerial attitude sensor MPU6000 comprises a 3-axis gyroscope and a 3-axis accelerometer. The 3-axis gyroscope and the 3-axis accelerometer respectively use three 16-bit analog-to-digital converters (ADCs) to convert a measured analog quantity into an outputable digital quantity. The aerial attitude sensor MPU6000 and peripheral components define a head motion detection module 3 to achieve the cursor movement and the cursor positioning of the patient display screen, so that the patient display screen is woken up and the scroll menu is activated by the cursor. The aerial attitude sensor MPU6000 comprises a first pin, a second pin, a third pin, a fourth pin, a fifth pin, a sixth pin, a seventh pin, an eighth pin, a ninth pin, a tenth pin, an eleventh pin, a twelfth pin, a thirteenth pin, a fourteenth pin, a fifteenth pin, a sixteenth pin, a seventeenth pin, an eighteenth pin, a nineteenth pin, a twentieth pin, a twenty-first pin, a twenty-second pin, a twenty-third pin, and a twenty-fourth pin. The first pin is an input of an optional external clock, the sixth pin is for inter-integrated circuit (I$^2$C) main serial data and is not used, the seventh pin is the I$^2$C main serial clock and is not used, the eighth pin is connected to the sixth pin of the Bluetooth module CC2540 to achieve SPI chip selection, the ninth pin is connected to the thirty-seventh pin of the Bluetooth module CC2540 output SPI serial data, the tenth pin is connected to a calibration filter capacitor, the eleventh pin is for frame synchronous digital input and is not used, the twelfth pin is for interrupting digital output and is not used, the thirteenth pin is a second power supply terminal, the eighteenth pin is power grounded, the nineteenth pin, the twenty-first pin, and the twenty-second pin are reserved and not used, the twentieth pin is connected to a capacitor of a charge pump, the twenty-third pin is connected to the fifth pin of the Bluetooth module CC2540 to achieve the SPI serial clock, the twenty-fourth pin is connected to the thirty-eighth pin of the Bluetooth module CC2540 to receive SPI serial data, and the second pin, the third pin, the fourth pin, the fifth pin, the fourteenth pin, the fifteenth pin, the sixteenth pin, and the seventeenth pin are not connected. The circuit enables the aerial attitude sensor MPU6000 to communicate with Bluetooth CC2540 through the SPI serial port. When the user moves his/her head, the aerial attitude sensor MPU6000 collects relative changes of head up, head down, head left, head right, and/or head inclined, and sends first signals generated based upon the relative changes to the computer so that the cursor on the patient display screen changes synchronously, so that the patient display screen is woken up and the scroll menu is activated by the cursor.

The Bluetooth module CC2540 and peripheral components define the communication module 5 to enable wireless communication to be achieved. The Bluetooth module CC2540 comprises a first pin, the fifth pin, the sixth pin, a tenth pin, the twentieth pin, a twenty-first pin, a twenty-second pin, a twenty-third pin, a twenty-fourth pin, a twenty-fifth pin, a twenty-sixth pin, a twenty-seventh pin, and a twenty-eighth pin, a twenty-ninth pin, a thirtieth pin, a thirty-first pin, a thirty-second pin, a thirty-third pin, and a thirty-fourth pin, the thirty-seventh pin, the thirty-eighth pin, a thirty-ninth pin, and a fortieth pin. The first pin is digitally grounded, the tenth pin and the thirty-ninth pin are digital power terminals, and the fortieth pin is power decoupled. The twenty-first pin, the twenty-fourth pin, the twenty-seventh pin, the twenty-eighth pin, the twenty-ninth pin, and the thirty-first pin are analog power ports, the fifth pin, the sixth pin, the thirty-seventh pin, and the thirty-eighth pin are SPI serial ports, the twentieth pin is a reset terminal, the twenty-second pin and the twenty-third pin are connected to a 32 MHz crystal oscillator, the thirty-second pin and the thirty-third pin are connected to a 32.768 KHz crystal oscillator, the twenty-fifth pin and the twenty-sixth pin are antenna terminals, the eighteenth pin is a code switch, the nineteenth pin is an indicator terminal, and the thirtieth pin is a reference current terminal.

The aerial attitude sensor MPU6000 and the photoelectric motion sensor A5030 communicate with the Bluetooth module CC2540 through the SPI serial ports. The aerial attitude sensor MPU6000 sends first signals corresponding to the cursor movement and the cursor positioning, and the photoelectric motion sensor A5030 sends second signals corresponding to the confirmation key. The Bluetooth modules sends the first signals and the second signals to the computer to wake up the patient display screen and activate the scroll menu, and one of the multiple call services of the scroll menu is selected.

In this embodiment, a schematic diagram of a circuit of the power supply module 6 of the call system body is shown in FIG. 3. A linear charge controller MCP73831 and peripheral circuits define a lithium battery charge circuit. The linear charge controller MCP73831 comprises a first pin, a second pin, a third pin, a fourth pin, a fifth pin, a sixth pin, a seventh pin, and an eighth pin. The first pin of the linear charge controller MCP73831 and the second pin of the linear charge controller MCP73831 are series connected and then connected to a power supply and a first end of a first capacitor C101. A second end of the first capacitor C101 is grounded so that input filtering is achieved. The third pin is series connected to a first resistor R101 and a light emitting diode D101 and then is series connected with the fourth pin and is power grounded, the fifth pin is not connected to anything, and the sixth pin is series connected to the seventh pin and the eighth pin through a second capacitor C102 so that output filtering is achieved. The power supply module 6 comprises a common cathode diode D102, which is configured to charge and supply power at the same time, the light emitting diode D101, which serves as a charging indicator, a power switch SW1 configured to switch the call system body switch to be opened and to be closed, and a battery interface BAT configured to connect to a battery. A voltage regulator RT9193 and peripheral circuits define a voltage regulator circuit. The voltage regulator RT9193 comprises a first pin and a second pin. The first pin of the voltage regulator RT9193 is an output end and is connected to a first end of each of two third capacitors C105 and C106 connected in parallel and a first end of a second resistor R102. A second end of the third capacitor C105 and a second end of the third capacitor C106 are connected to the ground, a second end of the second resistor R102 is connected to a fourth power supply terminal so that output filtering is achieved, and the second pin of the voltage regulator RT9193 is an input terminal and is connected to two fourth capacitors C102 and C103 connected in parallel so that input filtering is achieved. The power supply module 6 supplies power to the head motion detection module 3, the eyelid blinking detection module 4, and the communication module 5.

It will be apparent to those skilled in the art that various modifications and variation can be made in the present disclosure without departing from the spirit or scope of the invention. Thus, it is intended that the present disclosure cover the modifications and variations of this invention provided they come within the scope of the appended claims and their equivalents.

What is claimed is:

1. A call system for a patient, comprising:
    head-mounted device,
    a call system body,
    a patient display screen, and
    a nurse station display screen, wherein:
        the call system body comprises a head motion detection module, an eyelid blinking detection module, a communication module, and a power supply module,
        the head motion detection module collects relative changes of a head position through an aerial attitude sensor,
        first signals generated based upon the relative changes of the head position are sent to the patient display screen through a Bluetooth module of the communication module so that a cursor of the patient display screen changes synchronously,
        the cursor is configured to wake up the patient display screen and to activate a scroll menu,
        the eyelid blinking detection module collects a movement distance and a movement duration of an eyelid through a photoelectric motion sensor,
        second signals generated based upon the movement distance and the movement duration of the eyelid are sent to the patient display screen through the Bluetooth module of the communication module,
        the patient display screen is disposed on a patient bed and is above a head of the patient,
        the power supply module supplies power to the head motion detection module, the eyelid blinking detection module, and the communication module,
        when the movement distance of the eyelid reaches a preset distance and the movement duration of the eyelid is longer than a preset duration:
            a confirmation command is generated to select one of multiple call services in the scroll menu, and
            the one of the multiple call services selected by the patient is sent to the nurse station display screen by a wired network or a wireless network;
    wherein the head-mounted device comprises glasses, a hat, an earphone, a hair clip, a hair pin, or a headband, and
    at least a part of the call system body is detachably disposed on the head-mounted device.

2. The call system for the patient according to claim 1, wherein:
the call system body comprises a charging port, a power switch, an eyelid blinking detection sampling port, a Bluetooth code switch, a Bluetooth code indicator, and a head movement detection sampling port,
the charging port, the power switch, the Bluetooth code switch, and the Bluetooth code indicator are disposed on a side of the call system body, and
the eyelid blinking detection sampling port is disposed on a second side of the call system body directly facing an eye of the patient.

3. The call system for the patient according to claim 1, wherein the glasses have a frame and temples, a lower end of the call system body comprise a connection bracket, and the connection bracket is detachably disposed on at least one of the frame or the temples.

4. The call system for the patient according to claim 1, wherein the first signals generated based upon the relative changes of the head position comprise at least one of a head up signal, a head down signal, a head left signal, a head right signal, or a head inclined signal.

5. The call system for the patient according to claim 1, wherein:
the aerial attitude sensor comprises an eighth pin, a ninth pin, a twenty-third pin, a twenty-fourth pin, a tenth pin, a thirteenth pin, an eighteenth pin, and a twentieth pin,
the eighth pin is connected to the Bluetooth module for serial peripheral interface (SPI) chip selection,
the ninth pin is connected to the Bluetooth module to output SPI serial data,
the twenty-third pin is connected to the Bluetooth module to achieve an SPI serial clock,
the twenty-fourth pin is connected to the Bluetooth module to receive SPI serial data,
the tenth pin is connected to a calibration filter capacitor,
the thirteenth pin is a first power supply terminal connected to the power supply module,
the eighteenth pin is power grounded, and
the twentieth pin is connected to a capacitor of a charge pump.

6. The call system for the patient according to claim 1, wherein:
the photoelectric motion sensor comprises a first pin, a second pin, a third pin, a fourth pin, a fifth pin, a sixth pin, a seventh pin, and an eighth pin,
the first pin is connected to the Bluetooth module to output serial peripheral interface (SPI) serial data,
the third pin is connected to the Bluetooth module for resetting the photoelectric motion sensor,
the fourth pin is connected to the Bluetooth module for SPI chip selection,
the fifth pin is connected to the Bluetooth module to achieve an SPI serial clock,
the eighth pin is connected to the Bluetooth module to receive SPI serial data,
the second pin is a photodiode input terminal,
the sixth pin is power grounded, and
the seventh pin is a second power terminal connected to the power supply module.

7. The call system for the patient according to claim 1, wherein:
the patient display screen is a liquid crystal display (LCD) screen with a touch mode and a cursor mode,
the touch mode uses a window menu to display the multiple call services, and
the cursor mode uses the scroll menu.

8. The call system for the patient according to claim 1, wherein:
the photoelectric motion sensor and the aerial attitude sensor communicate through a serial peripheral interface (SPI) serial port of the Bluetooth module,
the Bluetooth module comprises a first pin, a tenth pin, a thirty-ninth pin, a fortieth pin, a twenty-first pin, a twenty-fourth pin, a twenty-seventh pin, a twenty-eighth pin, a twenty-ninth pin, a thirty-first pin, a fifth pin, a sixth pin, a thirty-seventh pin, a thirty-eighth pin, a twentieth pin, a twenty-second pin, a twenty-third pin, a thirty-second pin, a thirty-third pin, a twenty-fifth pin, a twenty-sixth pin, an eighteenth pin, a nineteenth pin, and a thirtieth pin,
the first pin is digital grounded,
the tenth pin and the thirty-ninth pin are digital power terminals,
the fortieth pin is power decoupled,
the twenty-first pin, the twenty-fourth pin, the twenty-seventh pin, the twenty-eighth pin, the twenty-ninth pin, and the thirty-first pin are analog power terminals,
the fifth pin, the sixth pin, the thirty-seventh pin, and the thirty-eighth pin are SPI serial ports,
the twentieth pin is a reset terminal,
the twenty-second pin and the twenty-third pin are connected to a 32 MHz crystal oscillator,
the thirty-second pin and the thirty-third pin are connected to a 32.768 KHz crystal oscillator,
the twenty-fifth pin and the twenty-sixth pin are antenna terminals,
the eighteenth pin is a code switch,
the nineteenth pin is an indicator terminal, and
the thirtieth pin is reference current terminal.

9. The call system for the patient according to claim 1, wherein:
the power supply module comprises a linear charge controller, a voltage regulator, a common cathode diode, a light emitting diode, a power switch, and a battery interface,
the linear charge controller comprises a first pin, a second pin, a third pin, a fourth pin, a sixth pin, a seventh pin, and an eighth pin,
the first pin of the linear charge controller and the second pin of the linear charge controller are series connected and then connected to a power supply and a first end of a first capacitor,
a second end of the first capacitor is grounded so that input filtering is achieved,
the third pin is series connected to a first resistor and the light emitting diode and then is series connected with the fourth pin and is power grounded,
the sixth pin is series connected to the seventh pin and the eighth pin through a second capacitor so that output filtering is achieved,
the common cathode diode is configured to charge and supply power at the same time,
the light emitting diode is a charging indicator,
the power switch is configured to switch the call system body to be opened and to be closed,
the battery interface is configured to connect to a battery,
the voltage regulator and peripheral circuits define a voltage regulator circuit,
the voltage regulator comprises a first pin and a second pin,
the first pin of the voltage regulator is connected to two third capacitors connected in parallel and a first end of a second resistor, a second end of the second resistor is connected to a fourth power supply terminal so that the output filtering is achieved, and the second pin of the voltage regulator is connected to two fourth capacitors connected in parallel so that input filtering is achieved.

\* \* \* \* \*